United States Patent [19]
Takahashi

[11] Patent Number: 6,093,753
[45] Date of Patent: Jul. 25, 2000

[54] SULFONIUM SALT COMPOUNDS, POLYMERIZATION INITIATOR, CURABLE COMPOSITION AND CURING METHOD

[75] Inventor: Eiji Takahashi, Ichihara, Japan

[73] Assignee: Nippon Soda Co., Ltd., Tokyo, Japan

[21] Appl. No.: 09/011,854

[22] PCT Filed: Aug. 21, 1996

[86] PCT No.: PCT/JP96/02333

§ 371 Date: Feb. 19, 1998

§ 102(e) Date: Feb. 19, 1998

[87] PCT Pub. No.: WO97/08141

PCT Pub. Date: Mar. 6, 1997

[30] Foreign Application Priority Data

Aug. 22, 1995 [JP] Japan ..................... 7-236140

[51] Int. Cl.$^7$ .................. C08F 2/50; C08F 4/72; C08L 63/00
[52] U.S. Cl. ................ 522/25; 522/31; 522/170; 522/181; 430/280.1; 430/281.1
[58] Field of Search ................. 522/25, 15, 31, 522/170, 181; 430/280.1, 281.1

[56] References Cited

U.S. PATENT DOCUMENTS

| | | | |
|---|---|---|---|
| 4,336,363 | 6/1982 | Crivello | 526/333 |
| 4,650,734 | 3/1987 | Molaire et al. | 430/7 |
| 5,013,814 | 5/1991 | Roth et al. | 528/90 |
| 5,047,568 | 9/1991 | Angelo et al. | 556/64 |
| 5,247,113 | 9/1993 | Roth et al. | 556/64 |

FOREIGN PATENT DOCUMENTS 405140209  6/1993  Japan ..................... 522/30

*Primary Examiner*—Susan W. Berman
*Attorney, Agent, or Firm*—Jacobson, Price, Holman & Stern, PLLC

[57] ABSTRACT

The present invention is to provide curable compositions usable appropriately in coatings, adhesives, photoresists, etc. and directed to sulfonium salt compounds represented by general formula [I];

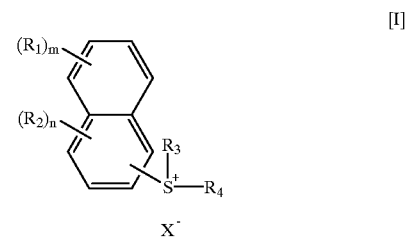

wherein $R_1$ and $R_2$ represent alkyl, hydroxy, alkoxy, alkylcarbonyl, aromatic carbonyl, aromatic thio or halogeno; $R_3$ represents alkyl; $R_4$ represents optionally substituted alkyl, alkenyl or cycloalkyl; m and n are each 0, 1, 2 or 3; and X represents a non-nucleophilic anionic residue; a cationic polymerization initiator containing the compound; and a curable composition which contains the compound and a cationically polymerizable compound optionally together with a sensitizer.

7 Claims, No Drawings

SULFONIUM SALT COMPOUNDS, POLYMERIZATION INITIATOR, CURABLE COMPOSITION AND CURING METHOD

FIELD OF THE INVENTION

The present invention is directed to novel sulfonium salt compounds, a cationic polymerization initiator containing the sulfonium salt compound, curable compositions containing the cationic polymerization initiator and a curing method, and more particularly to cationic curable compositions which cure in a short time even though the compositions are in various film states of which thickness being over wide range from very thin to thick, under heating or irradiation of activation energy rays, such as light, electronic rays and X-ray. Cured-products resulted from the said curable compositions have excellent physicochemical properties, and therefore, they are usable in coatings, adhesives, inks, photoresists, photosensitive resins for photomolding, etc.

BACKGROUND ART

In Japanese Patent Laid-open Nos. Sho 50-151997, Sho 50-158680 and Hei 2-178303, sulfonium salt compounds similar to the ones of the present invention are disclosed, wherein it is written that such sulfonium salt compounds can be used as an initiator to cure cationic polymerizable compounds, such as epoxy compounds, under light and radiations, such as electronic rays and X-ray.

However, the sulfonium salt compounds described in Japanese Patent Laid-open No. Sho 50-151997 is known as a highly photoactive polymerization initiator and is useful for curing transparent compositions, but it is not applicable for photomolding where long wavelength laser is used and photo curing of such compositions that contain high content of pigments, etc. because such sulfonium salt compounds have almost no absorption in a wavelength range longer than 360 nm, which is effective for ultraviolet radiation curing. In order to solve such problems, various studies on a sensitizer had been made, and several compounds, such as phenothiazine, anthracene and perilene, have been found out, however, those compounds were not yet satisfactory in such a purpose. Moreover, those compounds are unable to function as a thermal polymerization initiator so that it is hard to apply them for curing of thick films, and those compounds have other disadvantages, such as their complicated production process, high cost and low solubility in monomers. Whereas, the sulfonium salt compounds described in Japanese Patent No. Hei 2-178303 can work as a thermal polymerization initiator and is therefore capable of curing the thick films, however, their capability as a photo polymerization initiator is very weak and their solubility to monomers are low. Whereas, aliphatic sulfonium salt compounds reported by Endo et. al. in IUPAC MACRO 88 Prepr. 90 (1988) can also work as a thermal polymerization initiator and is therefore capable of curing the thick films, however, their capability as a photo polymerization initiator is very weak.

Therefore, it is an object of the present invention to provide a cationic polymerization initiator which is highly sensitive to heating, light, and irradiation of activation energy rays, such as electron rays and X-ray, particularly sensitive to light of which wavelength being longer than 360 nm, a cationic curable composition which is capable of curing in a short time in various film states of which thickness being over a wide range from very thin to thick, and the cured-product obtained therefrom shows to have excellent physicochemical properties and a curing method.

DISCLOSURE OF THE INVENTION

The present invention is directed to sulfonium salt compounds represented by a general formula [I];

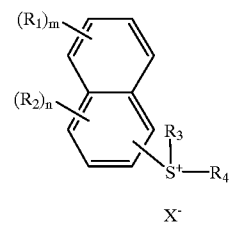

[I]

wherein $R_1$ and $R_2$ are each independently $C_{1-18}$ alkyl, hydroxy, $C_{1-18}$ alkoxy, $C_{1-18}$ alkylcarbonyl, aromatic carbonyl, aromatic thio or halogeno; $R_3$ is $C_{1-8}$ alkyl; $R_4$ is $C_{1-24}$ alkyl, provided $C_{1-24}$ alkyl has no substituent, or $R_4$ is $C_{5-24}$ alkyl, $C_{2-24}$ alkenyl or $C_{3-20}$ cycloalkyl, which may have a substituent, such as hydroxy, carbonyl, nitrile, phenyl, alkoxy, phenoxy, alkyleneoxy, halogen and indanyl; m and n are each independently 0, 1, 2 or 3; and X is a non-nucleophilic anionic residue; a cationic polymerization initiator, a cationically polymerizable compound and a curing method.

In the general formula [I], as the examples for $C_{1-18}$ alkyl represented by $R_1$ and $R_2$, methyl, ethyl, propyl, isopropyl, butyl, isobutyl, t-butyl, decyl, dodecyl and the like are given, as the examples for the $C_{1-18}$ alkoxy, methoxy, ethoxy, propoxy, butoxy, hexyloxy, decyloxy, dodecyloxy and the like are given, as the examples for the $C_{1-18}$ alkylcabonyl, acetoxy, propionyloxy, decylcarbonyloxy, dodecylcarbonyloxy and the like are given, as the examples for the aromatic carbonyl, benzoyloxy and the like are given, as the examples for the aromatic thio, phenylthio and the like are given, as the examples for the halogeno, fluorine, chlorine, bromine, iodine and the like are given, as the examples for the $C_{1-8}$ alkyl represented by $R_3$, methyl, ethyl, propyl, isopropyl, butyl, isobutyl, t-butyl, amyl, hexyl and the like are given, and as the examples for the substituent represented by $R_4$, pentyl, decyl, dodecyl, 2-phenylethyl, 2-phenylpropyl, 2-phenoxyethyl, 2-phenyl-2-hydroxyethyl, 2-phenyl-2-acetoxyethyl, 2-phenyl-2-methoxyethyl, 2-methoxycarbonylethyl, 3-hydroxypropyl, 2-methoxycarbonylpropyl, cyclohexyl, 2-hydroxycyclohexyl, cyclopentyl, 2-indanyl, 1-hydroxy-2-indanyl, 1-acenaphthenyl, bicyclononyl, norbotnyl, cumarinyl, dihydrobenzofuranyl, allyl, 2-butenyl, cinnamyl, 1-carboxyethyl, 1-methoxycarbonylethyl, 1-ethoxycarbonylethyl, 1-(n-propoxycarbonyl)ethyl, 1-(isopropoxycarbonyl)ethyl, 1-(3-chloro-2-hydroxypropoxycarbonyl) ethyl, 1-(3-acetoxy-2-hydroxypropoxycarbonyl)ethyl, 1-(3-methacryloyloxy-2-hydroxypropoxycarbonyl)ethyl, 1-(3-benzoyloxy-2-hydroxypropoxycarbonyl)ethyl, 1-(3-chloro-2-acetoxypropoxycarbonyl) ethyl, 1-(n-butoxycarbonyl)ethyl, 1-dodecyloxycarbonylethyl, 1-phenoxycarbonylethyl, 1-benzyloxycarbonylethyl, 1-(N-methyl-4-methoxycarbonylanilinocarbonyl)ethyl, 1-carboxypropyl, 1-methoxycarbonylpropyl, 1-ethoxycarbonylpropyl, 1-dodecyloxycarbonylpropyl, 1-carboxybutyl, 1-methoxycarbonylbutyl, 1-ethoxycarbonylbutyl, 1-dodecyloxycarbonylbutyl, 1-carboxypentyl, 1-methoxycarbonylpentyl, 1-ethoxycarbonylpentyl, 1-dodecyloxycarbonylpentyl, α-ethoxycarbonylbenzyl, phenacyl, 1-benzoylethyl, cyanomethyl, 1-cyanoethyl, ethoxycarbonylacetylmethyl, 2-indanyl, 2-cyclohexanonyl, canfer, γ-butyrolactonyl and the like are given.

In the sulfonium salt compounds according to the present invention, the compounds which contains two sulfonium salt structures in one molecule of the sulfonium salt compound are also included, and as the examples for them, the compounds represented by the following general formulas [II] and [III] are given.

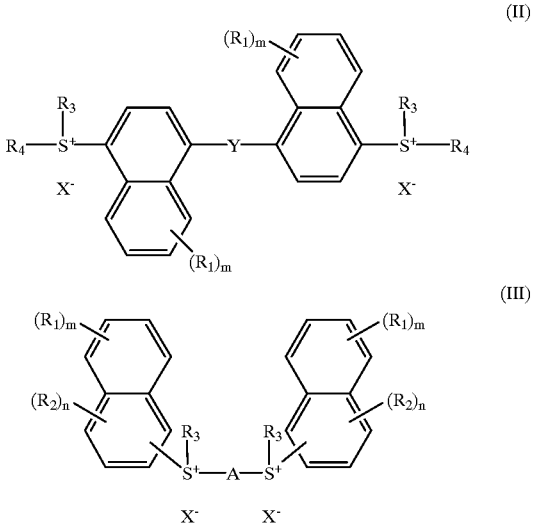

wherein Y represents oxygen or sulfur, and A is cycloalkylene, phenylene, alkylene or alkenylene, and these groups may have any of hydroxy, carbonyl and ester or ether linkage.

The sulfonium salt compounds of the present invention can be manufactured according to the following reaction formula.

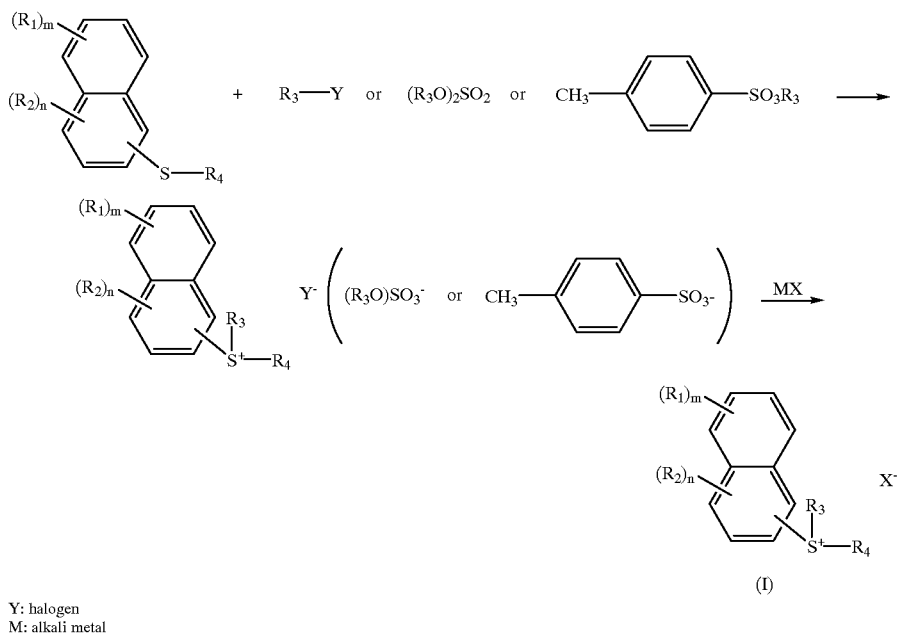

Y: halogen
M: alkali metal

The reaction above is carried out at temperature of from a room temperature to 150° C., and preferably from 40 to 90° C. for 1 to several dozen of hours, in an organic solvent, such as acetonitrile, dioxane and ethanol, if required. After completion of this reaction, the reacted-solution was mixed with water and MX and then stirred. The product precipitated was either taken out by filtration or extracted with an organic solvent to obtain the objective product.

The sulfonium salt compounds according to the present invention can cure a cationic polymerizable compound under not only heat but also an irradiation of activation energy rays, such as light, electron rays and X-ray.

Among the compounds represented by a general formula [I] of the present invention, the sulfonium salt compounds wherein $R_4$ is $C_8$–$C_{24}$ alkyl, alkyl having an aromatic ring on a carbon locating at the β-position of a sulfur atom, cycloalkyl or indanyl, is preferable in term of solubility to monomers.

As the examples of $R_4$ described above, decyl, dodecyl, 2-phenylethyl, 2-phenylpropyl, 2-phenoxyethyl, 2-phenyl-2-hydroxyethyl, 2-phenyl-2-acetoxyethyl, 2-phenyl-2-methoxyethyl, cyclohexyl, 2-hydroxycyclohexyl, cyclopentyl, 2-indanyl, 1-hydroxy-2-indanyl, 1-acenaphthenyl, bicyclononyl, norbornyl, cumarinyl and dihydrobenzofuranyl are given.

Furthermore, among the compounds represented by the general formula [I] of the present invention, the sulfonium salt compound wherein $R_4$ is a group represented by either of the following general formulas;

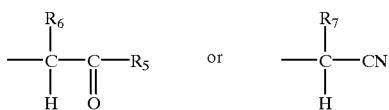

wherein $R_5$ is $C_{1-24}$ alkyl, $C_{2-24}$ alkenyl, $C_{3-20}$ cycloalkyl, $C_{1-24}$ alkoxy, phenyl, naphthyl or amino, and each may have a substituent, such as hydroxy, carbonyl, nitrile, phenyl, alkoxy, phenoxy, alkyleneoxy, halogeno and nitro, $R_6$ and $R_7$ are each independently hydrogen, $C_{1-8}$ alkyl or phenyl, and $R_5$ and $R_6$ may jointly form a ring optionally substituted with hydroxy, carbonyl, nitrile, phenyl, alkoxy, phenoxy or alkyleneoxy, or $R_5$ and $R_6$ may jointly form indanone, or $R_5$ may have hydrogen if $R_6$ is not hydrogen, m and n are each independently 0, 1, 2 or 3, and X represents a non-nucleophilic anionic residue, show to have remarkably-improved photo reactivity particularly in combination with a sensitizer, and they are suitable for curing pigment-containing curable compositions.

As the examples of a group represented by $R_5$ shown above, hydroxy, methoxy, ethoxy, n-propoxy, isopropoxy, 3-chloro-2-hydroxypropoxy, 3-acetoxy-2-hydroxypropoxy, 3-metacryloyloxy-2-hydroxypropoxy, 3-benzoyloxy-2-hydroxypropoxy, 3-chloro-2-acetoxypropoxy, n-butoxy, 1-dodecyloxy, phenoxy, benzyloxy, N-methyl-4-methoxycarbonylanilino, phenyl, ethoxycarbonyloxymethyl and the like are given.

As the examples of the non-nucleophilic residue represented by X, $SbF_6$, $AsF_6$, $PF_6$ and $BF_4$ are preferably given.

Now, the representative examples of the sulfonium salt compounds according to the present invention are shown below, provided that X in the formula represents a non-nucleophilic residue, such as $SbF_6$, $AsF_6$, $PF_6$ and $BF_4$.

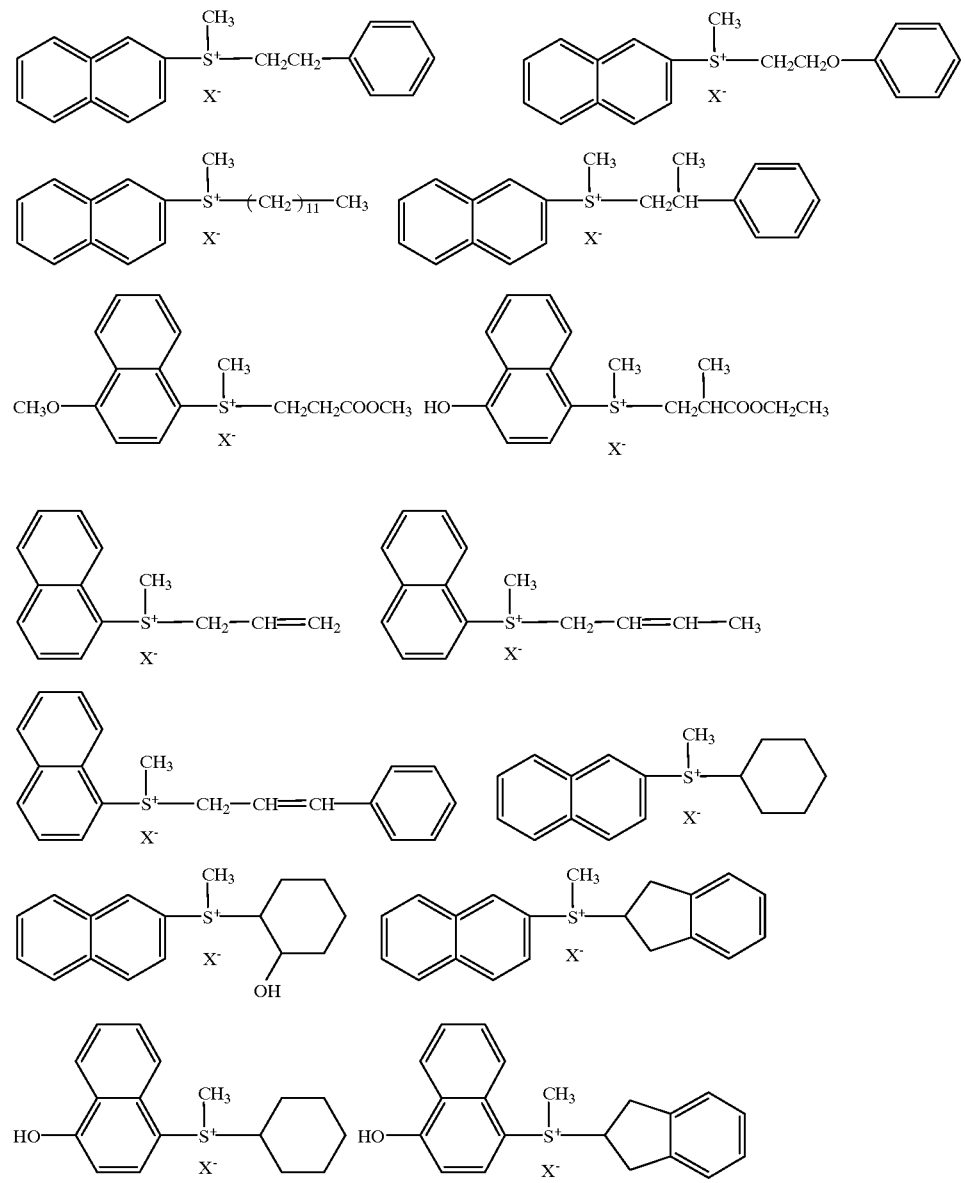

-continued
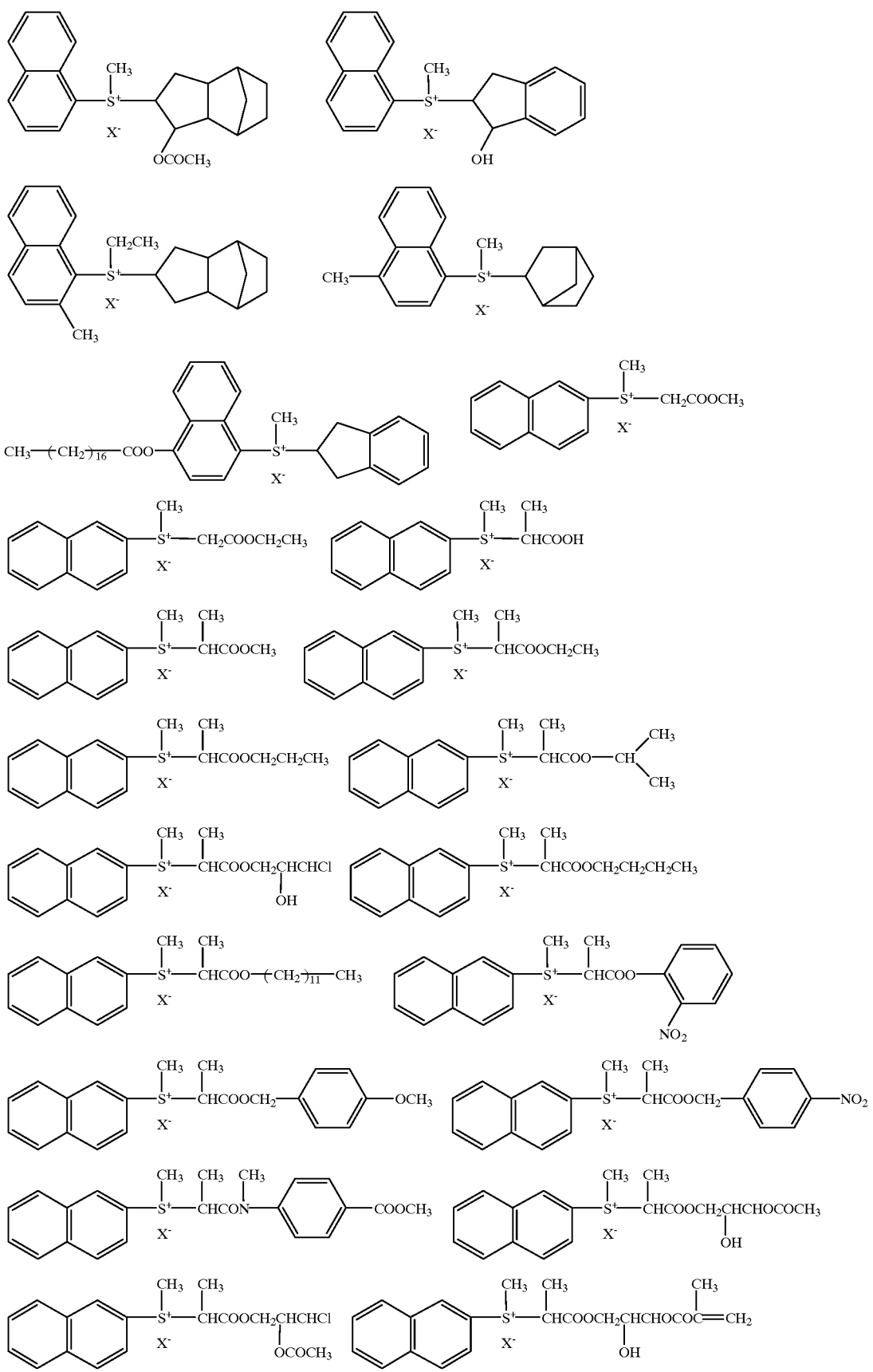

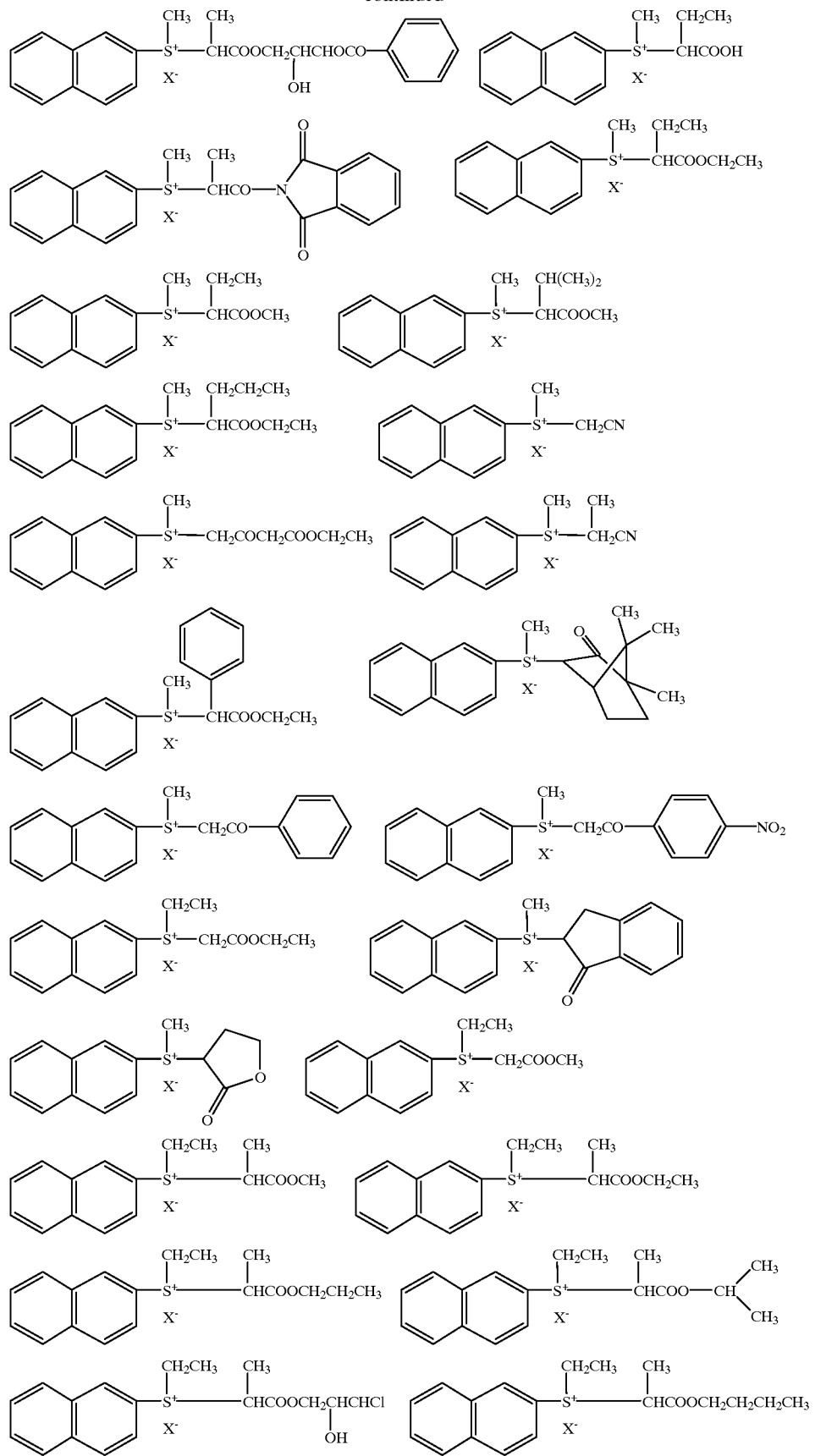

-continued
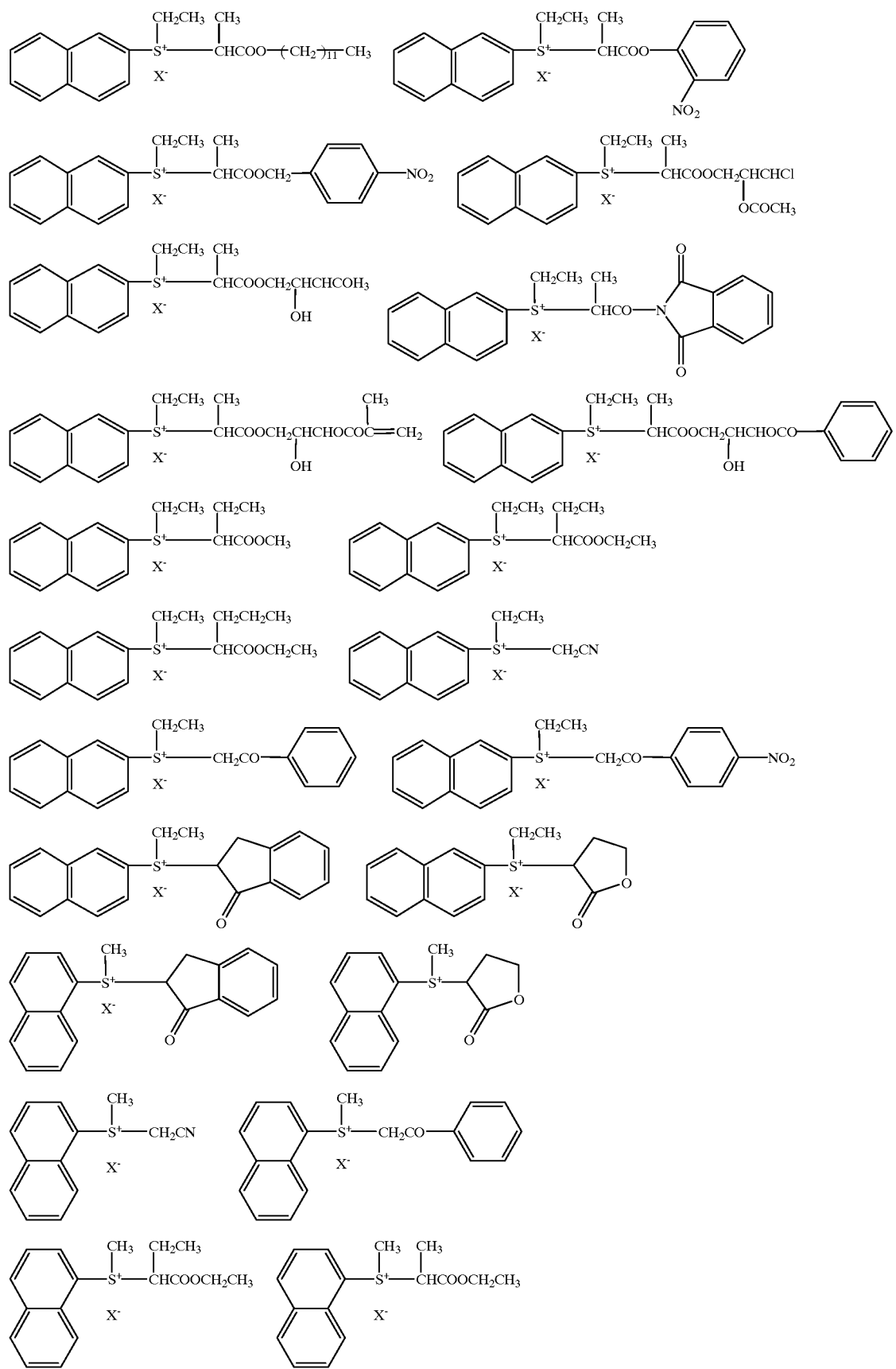

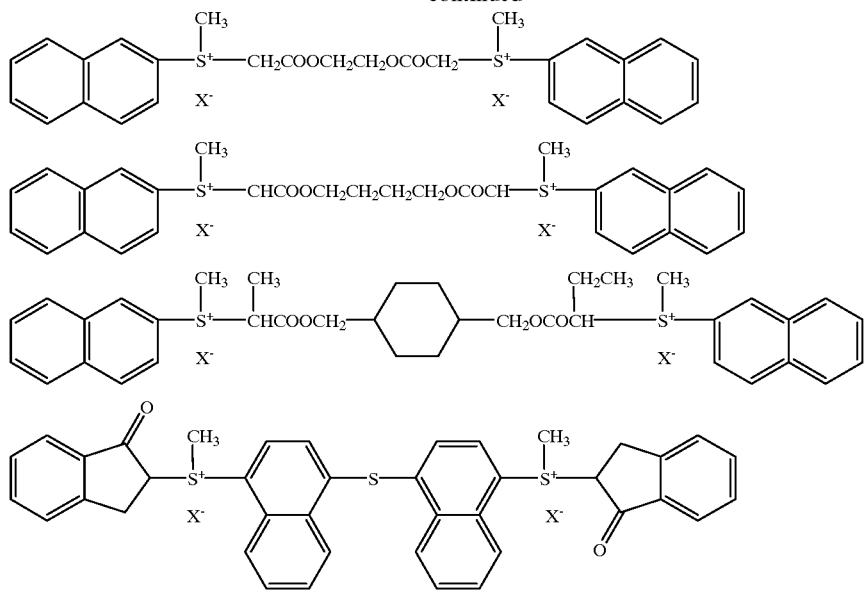

The sulfonium salt compounds of the present invention are usable in combination with a sensitizer, and the compounds can develop curing in remarkably short time in such combination use. In addition, the sulfonium salt compounds of the present invention are very useful for curing of curable compositions which contain a pigment, such as titanium dioxide.

The sensitizer used in the present invention is a compound which accelerates photo reactions of the sulfonium salt compounds as described above. For example, a compound which easily releases hydrogen radicals, radical polymerization inhibitors, a compound to react with a sulfonium salt compound during photo reaction process of the solfonium salt compound to release protons as a result, an electron donor, etc. are exemplified as the sensitizer. Concretely, as the sensitizer usable in the present invention, thiol compounds, compounds easily release protons, such as hydrocarbons, phenol derivatives, such as 4-methoxy phenol, 4-benzyloxy phenol, 4-methoxy-2-(t-butyl)phenol, hydroquinone, 4-methoxy-1-naphthol and 2-hydroxydibenzofuran, naphthol derivatives, such as 1-naphthol, 2-naphthol, 1-methoxynaphthalene, 2-methoxynaphthalene, 1-hydroxyphenathlene, glycidyl-1-naphthyl ether, 2-(2-naphthoxy)ethyl vinyl ether, 1,4-dihydroxy naphthalene, 1,5-dihydroxy naphthalene, 1,6-dihydroxy naphthalene, 2,7-dihydroxy naphthalene, 2,7-dimethoxy naphthalene, 1,1'-thiobis(2-naphthol), 1,1'-bi-2-naphthol, 1,5-naphthyl diglycidyl ether, 2,7-di(2-vinyloxyethyl) naphthyl ether, 4-methoxy-1-naphthol, ESN-175 (epoxy resin produced by Shinnittetsu Chemical Co., Ltd.) or its series, formalin condensates of naphthol derivatives, radical polimerization inhibitors, such as phenothiazine, quinones, such as naphthoquinone, anthraquinone, 2-ethyl anthraquinone, 2-t-butyl anthraquinone, 2-hydroxymethyl anthraquinone, 2,3-dimethyl anthraquinone, naphthacenequinone, 9,10-phenanthrenequinone and canferquinone, thio xanthone derivatives, such as 9,10-dimethoxy anthracene, 2-ethyl-9,10-dimethoxy anthracene, 2-t-butyl-9,10-dimethoxy anthracene, 2,3-dimethyl-9,10-dimethoxy anthracene, 9-methoxy-10-methyl anthracene, 1,4-dimethoxy chrycene, 9,10-diethoxy anthracene, 2-ethyl-9,10-diethoxy anthracene, 2-t-butyl-9,10-diethoxy anthracene, 2,3-dimethyl-9,10-diethoxy anthracene, 9-ethoxy-10-methyl anthracene, 1,4-diethoxy chrycene, 9,10-dipropoxy anthracene, 2-ethyl-9,10-dipropoxy anthracene, 2-t-butyl-9,10-dipropoxy anthracene, 2,3-dimethyl-9,10-dipropoxy anthracene, 9-isopropoxy-10-methyl anthracene, 1,4-dipropoxy chrycene, 9,10-dibenzyloxy anthracene, 2-ethyl-9,10-dibenzyloxy anthracene, 2-t-butyl-9,10-dibenzyloxy anthracene, 2,3-dimethyl-9,10-dibenzyloxy anthracene, 9-benzyloxy-10-methyl anthracene, 1,4-dibenzyloxy chrycene, 9,10-di-α-methylbenzyloxy anthracene, 2-ethyl-9,10-di-α-methylbenzyloxy anthracene, 2-t-butyl-9,10-di-α-methylbenzyloxy anthracene, 2,3-dimethyl-9,10-di-α-methylbenzyloxy anthracene, 9-(α-methylbenzyloxy)-10-methyl anthracene, 1,4-di-α-methylbenzyloxy chrycene, 9-hydroxy phenathrane, xanthone, thio xanthone and 2,4-diethylthio xanthone, carbazole derivatives, such as carbazole, N-vinyl carbazole and N-ethyl carbazole, aromatic amine compounds, such as N,N-diphenyl-p-phenylene diamine and compounds represented by the following general formula [IV];

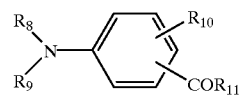

(IV)

wherein $R_8$ and $R_9$ are each independently same or different straight or branched chain $C_1$–$C_{20}$ alkyl, or $R_8$ and $R_9$ may bind into one unit, $R_{10}$ is hydrogen, lower alkyl or halogen, $R_{11}$ is hydrogen, hydroxy, optionally substituted alkyl, optionally substituted phenyl, optionally substituted benzyl, optionally substituted alkoxy, optionally substituted phenoxy or optionally substituted benzyloxy, are given as the examples.

As the examples of the compound represented by a general formula [IV] described above, p-dimethylamino benzoate, p-dimethylamino benzaldehyde, ethyl p-dimethylamino benzoate, (2-n-butoxyethyl) p-dimethylamino benzoate, isoamyl p-dimethylamino benzoate, p-dimethylamino acetophenone, p-diethylamino benzoate, p-diethylamino benzaldehyde, etc. can be given.

Among the sensitizer as described above, as preferable examples for the combination with a cationic polymerization initiator, anthraquinone derivatives, such as phenothiazine and 2-ethyl anthraquinone, 9,10-dialkoxy anthracene derivatives, such as 9,10-dimethoxy anthracene, 9,10-diethoxy anthracene and 2-ethyl-9,10-dimethoxy anthracene, thio xanthone derivatives, thio xanthone, isopropylthio xanthone, 2,4-dimethylthio xanthone, 2,4-diethylthio xanthone, 2,4-isopropylthio xanthone and 2-chlorothio xanthone, carbazole derivatives, such as N-ethyl carbazole, naphthalene derivatives having at least one hydroxy or alkoxy, such as 1-naphthol and 2-methoxy naphthalene, can be given.

As the cationic polymerizable compounds to be used in the present invention, the followings can be used.

(a) The following vinyl compounds can be used as the cationic polymerizable compound, which includes, alkyl vinyl ether compounds, such as methyl vinyl ether, n-butyl vinyl ether, ethyl vinyl ether, isobutyl vinyl ether, cyclohexyl vinyl ether, 2-chloroethyl vinyl ether, 2-phenoxyethyl vinyl ether, 2-hydroxyethyl vinyl ether, 4-hydroxybutyl vinyl ether, stearyl vinyl ether and 2-acetoxyethyl vinyl ether, alkenyl vinyl ether compounds, such as aryl vinyl ether, 2-metacryloyloxyethyl vinyl ether and 2-acryloyloxyethyl vinyl ether, allyl vinyl ether compounds, such as phenyl vinyl ether and p-methoxyphenyl vinyl ether, cationic polymerizable nitrogen-containing compounds, such as N-vinyl carbazole and N-vinyl pyrrolidone, multifunctional vinyl compounds, such as butanediole divinyl ether, triethylene glycol divinyl ether, cyclohexanediole divinyl ether, 1,4-benzenedimethanol divinyl ether, hydroquinone divinyl ether and sazolcinol divinyl ether.

(b) The following epoxy compounds can be used as the cationic polymerizable compound, which includes, monofunctional monomers, such as phenylglycidyl ether, p-tert-butylphenylglycidyl ether, butylglycidyl ether, 2-ethylhexylglycidyl ether, allylglycidyl ether, 1,2-butylene oxide, 1,3-butadiene monoxide, 1,2-dodecylene oxide, epichlorohydrin, 1,2-epoxy decane, ethylene oxide, propylene oxide, stylene oxide, cyclohexene oxide, 3-metacryloyloxymethyl cyclohexene oxide, 3-acryloyloxymethyl cyclohexene oxide, 3-vinyl cyclohexene oxide and 4-vinyl cyclohexene oxide, and multifunctional epoxy compounds, such as 1,1,3,-tetradecadiene oxide, limonene dioxide, 3,4-epoxycyclohexylmethyl-(3,4-epoxycyclohexyl)carboxylate, di(3,4-epoxycyclohexyl) azipate, phenyl glycidyl ether, bisphenol A epoxy resin, bisphenol F epoxy resin, o-, m-, p-cresol novolac epoxy resin, phenol novolac epoxy resin and polyglycidyl ethers of polyhydric alcohols.

(c) The following bicyclo-ortho esters can be used as the cationic polymerizable compound, which includes, 1-phenyl-4-ethyl-2,6,7-trioxabicyclo[2,2,2]octane, 1-ethyl-4-hydroxymethyl-2,6,7-trioxabicyclo[2,2,2]octane, etc.

(d) The following spiro-ortho carbonates can be used as the cationic polymerizable compound, which includes, 1,5,7,11-tetraoxaspiro[5,5]undecane, 3,9-dibenzyl-1,5,7,11-tetraoxaspiro[5,5]undecane, 1,4,6-trioxaspiro[4,4]nonane, 2-methyl-1,4,6-trioxaspiro[4,4]nonane, 1,4,6-trioxaspiro[4,5]decane, etc.

Moreover, these compounds recited above can be used either alone or in combination of 2 or more of the compounds. In particular, the sulfonium salt compounds according to the present invention are suitable for curing alicyclic epoxy compounds and vinyl ether compounds.

In the present invention, the combining ratio of the Sulfonium salt compound represented by the general formula [I] relative to 100 parts of the cationic polymerizable compound is 0.01–20 parts, and preferably 0.1–10 parts. If the rate of the sulfonium salt compound is too low, the curing capability of the cationic polymerizable compound deteriorates, while the property of the cured-product deteriorates if the rate of the sulfonium salt compound is too much.

Whereas, the combining ratio of the sensitizer described above relative to 100 parts of the cationic polymerizable compound is 0.001–10 parts, and preferably 0.01–5 parts. If the rate of the sensitizer is too small, the photo reactivity of the sulfonium salt compound deteriorates, while the property of the composition deteriorates if the rate of the sensitizer is too much.

The curable composition according to the present invention can easily cure under light.

For the curing under light, light of which wavelength is 500 nm or less, particularly ultraviolet radiation, is preferably used, and therefore, low-pressure mercury lamps, medium-pressure mercury lamps, high-pressure mercury lamps, superhigh-pressure mercury lamps, metal halide lamps, xenon lamps, carbon arc lamps and the like are used as the light source. For this purpose, laser, such as semiconductor laser, argon laser and He—Cd laser, can be used as well. In particular, when using light for curable compositions containing a pigment, such as titanium dioxide, it is preferable to use a metal halide lamp containing gallium.

Also, the curable compositions according to the present invention can easily cure under ionizing radiations, such as α rays, β rays, γ rays, neutron rays, X-ray and accelerated electron rays. In case of the curing by ionizing radiations, the radiation in a dose range of from 0.5 to 60 Mrad can be used normally, and preferably from 1 to 50 Mrad.

The curable compositions according to the present invention can easily cure under heat. The heating should be applied in a temperature range of from 80 to 250° C., and preferably from 100 to 200° C. It is also possible for the curable compositions to cure under light, ionizing radiations and heating in combination.

BEST MODE FOR CARRYING OUT THE INVENTION

Now, the present invention is further described in detail with referring to the examples described hereinbelow, however, it should be noted that the present invention shall not be limited to the scope as described in the following examples.

EXAMPLE 1

Preparation of 2-naphthyl(2-indanyl)methyl sulfonium hexafluorophosphate:

2-naphthyl(2-indanyl)sulfide in an amount of 27.64 g and dimethyl sulfuric acid in an amount of 13.24 g were mixed and allowed to a reaction at 50° C. for 10 hours. The reacted-mixture was then dissolved into distilled water in an amount of 100 g, mixed with potassium hexafluorophosphate in an amount of 18.41 g and then stirred vigorously.

The precipitate obtained was washed with water and dried at 40° C. under reduced pressure to obtain the objective compound. The yield was 81%.

EXAMPLE 2

Preparation of 2-naphthyl-2-phenylpropylmethyl sulfonium hexafluorophosphate:

2-naphthyl-2-phenylpropyl sulfide in an amount of 27.84 g and dimethyl sulfuric acid in an amount of 13.24 g were mixed and allowed to a reaction at 50° C. for 10 hours. The reacted-mixture was then dissolved into distilled water in an amount of 100 g, mixed with potassium hexafluorophosphate in an amount of 18.41 g and then stirred vigorously. The precipitate obtained was extracted with ethyl acetate, and the extract was washed with water and dried at 40° C. under reduced pressure following to the removal of the ethyl acetate remained to obtain the objective compound. The yield was 86%.

EXAMPLE 3

Preparation of 2-naphthyldodecylmethyl sulfonium hexafluorophosphate:

2-naphthyldodecyl sulfide in an amount of 32.86 g and dimethyl sulfuric acid in an amount of 13.24 g were mixed and allowed to a reaction at 80° C. for 1 hour and subsequently at 50° C. for 10 hours. The reacted-mixture was then dissolved into distilled water in an amount of 100 g, mixed with potassium hexafluorophosphate in an amount of 18.41 g and then stirred vigorously. The precipitate obtained was extracted with ethyl acetate, and the extract was washed with water and dried at 40° C. under reduced pressure following to the removal of ethyl acetate remained to obtain the objective compound. The yield was 93%.

EXAMPLE 4

Preparation of 2-naphthylethoxycarbonylmethylmethyl sulfonium hexafluorophosphate:

2-naphthylethoxycarbonylmethyl sulfide in an amount of 24.63 g and dimethyl sulfuric acid in an amount of 13.24 g were mixed and allowed to a reaction at 80° C. for 10 hours. The reacted-mixture was then dissolved into a mixed solution of distilled water in an amount of 300 ml and ethyl acetate in an amount of 100 ml and stirred. The aqueous layer resulted was taken out, mixed with potassium hexafluorophosphate in an amount of 18.41 g and ethyl acetate in an amount of 300 ml and then stirred. The ethyl acetate layer was then washed with 100 ml of distilled water twice and mixed with anhydrous magnesium sulfate to remove water remained in the ethyl acetate layer. After evaporating ethyl acetate from the ethyl acetate layer, the residue was allowed to dry at 40° C. under reduced pressure to obtain the objective compound. The yield was 36.4 g.

EXAMPLES 5 THROUGH 27

The objective compounds were prepared according to the method similar to the examples described above.

The examples of the sulfonium salt compounds according to the present invention are shown in Table 1.

TABLE 1

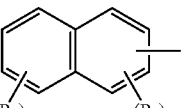

| Example | $(R_1)_m$ | $(R_2)_m$ | $R_3$ | $R_4$ | X | IR (cm$^{-1}$) |
|---|---|---|---|---|---|---|
| 1 | 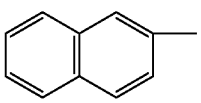 | | CH$_3$ | 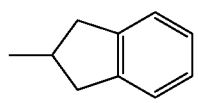 | PF$_6$ | 3063, 2944, 1481, 1414, 1078, 984, 876, 836, 808, 764, 558 |
| 2 | 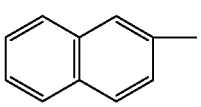 | | CH$_3$ | —CH$_2$—CH(CH$_3$)—C$_6$H$_5$ | PF$_6$ | 2973, 1496, 1455, 1422, 839, 765, 704, 559 |
| 3 | 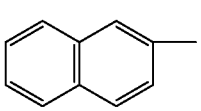 | | CH$_3$ | —(CH$_2$)$_{11}$CH$_3$ | PF$_6$ | 2926, 2855, 1467, 1424, 1076, 987, 839, 751, 559 |
| 4 | 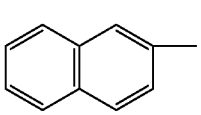 | | CH$_3$ | —CH$_2$COOCH$_2$CH$_3$ | PF$_6$ | 3006, 2952, 1725, 1313, 1201, 1076, 831 |
| 5 | 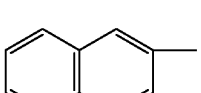 | | CH$_3$ | —CH(CH$_3$)COOH | PF$_6$ | 3043, 2955, 1737, 1433, 1273, 1076, 835 |
| 6 | 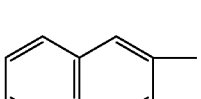 | | CH$_3$ | —CH(CH$_3$)COOCH$_3$ | PF$_6$ | 3042, 2956, 1737, 1455, 1316, 1207, 1077, 840 |
| 7 | 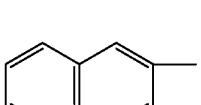 | | CH$_3$ | —CH(CH$_3$)COOCH$_2$CH$_3$ | PF$_6$ | 3041, 2947, 1730, 1455, 1313, 1198, 1077, 842 |

TABLE 1-continued

| Example | (R₁)ₘ / (R₂)ₘ naphthalene | R₃ | R₄ | X | IR (cm⁻¹) |
|---|---|---|---|---|---|
| 8 | naphthalene (2-yl) | CH₃ | —CH(CH₃)COOCH₂CH₃ | PF₆ | 3042, 2972, 1732, 1460, 1317, 1196, 1076, 840 |
| 9 | naphthalene (2-yl) | CH₃ | —CH(CH₃)COOCH(CH₃)₂ | PF₆ | 3042, 2986, 1727, 1456, 1311, 1201, 1076, 840 |
| 10 | naphthalene (2-yl) | CH₃ | —CH(CH₃)COOCH₂CH₂CH₃ | PF₆ | 3042, 2963, 1732, 1459, 1313, 1194, 1079, 840 |
| 11 | naphthalene (2-yl) | CH₃ | —CH(CH₃)COO—(CH₂)₁₁—CH₃ | PF₆ | 3035, 2926, 2855, 1734, 1459, 1250, 1196, 1076, 844 |
| 12 | naphthalene (2-yl) | CH₃ | —CH(CH₃)COO—(CH₂)₁₁—CH₃ | SbF₆ | 3035, 2926, 2855, 1734, 1458, 1245, 1196, 1076, 661 |
| 13 | naphthalene (2-yl) | CH₃ | —CH(CH₂CH₃)COOCH₃ | PF₆ | 3041, 2947, 1738, 1357, 1273, 1076, 839 |
| 14 | naphthalene (2-yl) | CH₃ | —CH(CH₂CH₃)COOCH₂CH₃ | PF₆ | 3042, 2945, 1732, 1260, 1191, 1013, 840 |
| 15 | naphthalene (2-yl) | CH₃ | —CH(CH₃)COO—(2-NO₂-C₆H₄) | PF₆ | 3045, 2954, 1762, 1531, 1353, 1211, 1160, 836 |
| 16 | naphthalene (2-yl) | CH₃ | —CH(CH₃)COOCH₂CH(OH)CH₂Cl | PF₆ | 3583, 3040, 2947, 1741, 1455, 1313, 1191, 1077, 840 |
| 17 | naphthalene (2-yl) | CH₃ | —CH(CH₃)COOCH₂—(4-OCH₃-C₆H₄) | PF₆ | 3035, 2947, 1737, 1512, 1459, 1249, 1076, 840 |
| 18 | naphthalene (2-yl) | CH₃ | —CH(CH₃)COOCH₂—(4-NO₂-C₆H₄) | PF₆ | 3040, 2947, 1742, 1523, 1349, 1186, 1076, 840 |

TABLE 1-continued

| Example | (R₁)ₘ / (R₂)ₘ | R₃ | R₄ | X | IR (cm⁻¹) |
|---|---|---|---|---|---|
| 19 | 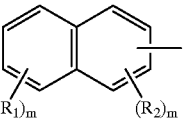 | CH₃ | 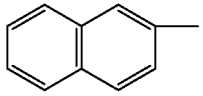 | PF₆ | 3066, 2955, 1780, 1385, 1219, 1170, 838 |
| 20 | 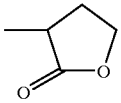 | CH₃ | —CH₂CN | PF₆ | 3047, 2950, 1421, 1076, 834 |
| 21 | 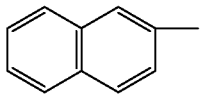 | CH₃ | —CH₂COCH₂COOCH₂CH₃ | PF₆ | 3036, 2945, 1746, 1724, 1373, 1201, 839 |
| 22 | 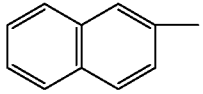 | CH₃ | 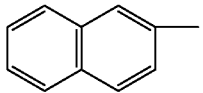 | PF₆ | 3058, 2961, 1681, 1452, 1302, 1211, 979, 838 |
| 23 | 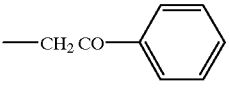 | CH₃ | 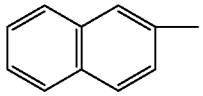 | PF₆ | 3055, 2942, 1689, 1531, 1349, 1209, 835 |
| 24 | 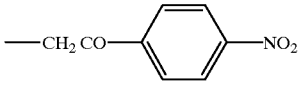 | CH₃ | 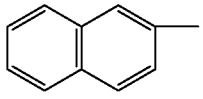 | PF₆ | 3043, 2943, 1717, 1467, 1277, 837 |
| 25 | 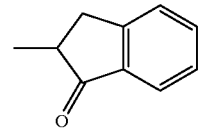 | CH₃ | 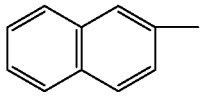 | PF₆ | 2965, 1749, 1273, 1192, 843 |
| 26 | 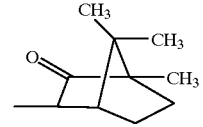 | CH₃ | 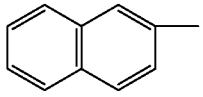 | PF₆ | 3035, 2947, 1744, 1719, 1437, 1270, 840 |
| 27 | 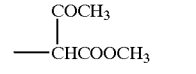 | CH₃ | 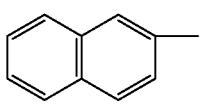 | PF₆ | 3035, 2946, 1723, 1655, 1456, 1272. 1078, 840 |

TEST EXAMPLE 1

Transparent-type curable composition (1) Photo curing Property Test

A sensitizer, 2,4-diethylthio xanthone (2,4-DETX) and a sulfonium salt compound were dissolved in γ-butylolactone, and the mixture was mixed to 100 parts of ERL-4211 (Alicyclic epoxy compound manufactured by UCC) at a rate of 1.0 part and 2.0 parts, respectively, to prepare a composition. The composition obtained was applied onto a tin plate to form a film of the composition of 3 μm thickness, and the film was allowed for curing under the following conditions. In this test, the composition which cured and became tack-free was represented by ○ mark, the composition which cured but remained tack or did not cure were represented by × mark.

UV Irradiation Apparatus: Belt Conveyer-type UV Irradiation Apparatus

Lamp: 2 Kw(80 w/cm) High-pressure mercury lamps arranged in parallel

Conveyer Speed: 10 m/min.

Times of Irradiation: 1

(2) Heat Curing Property Test 0.5 g of the composition obtained as described above was weighed and placed in a sample vessel, and the vessel was put in an oven maintained at 150° C. After heating, the composition which cured was represented by ○ mark, while the one which did not cure was represented by × mark. The result was shown in Table 2.

(3) Storage Stability Test 100 g of the composition obtained as described above was weighed in a sample vessel and the vessel was placed in an oven maintained at 25° C. for one month. After that, the composition of which viscosity is less than 2 times of the initial viscosity was represented by ○ mark, while the one of which viscosity changed to more than 2 times of the initial viscosity or the one cured were represented by × mark. The result was shown in Table 2.

TABLE 2

| Sulfonium salt | Sensitizer | Photo curing | Heat Curing | Stability |
| --- | --- | --- | --- | --- |
| Example 1 | — | ○ | ○ | ○ |
| Example 1 | 2,4-DETX | ○ | ○ | ○ |
| Example 4 | — | ○ | ○ | ○ |
| Example 4 | 2,4-DETX | ○ | ○ | ○ |
| Reference Exp. 1 | — | × | ○ | × |
| Reference Exp. 2 | — | ○ | × | ○ |

Note:
Reference Compound 1 [Compound disclosed in IUPAC MACRO 88 Prepr. 90(1988)]

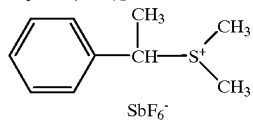

Reference Compound 2 [Compound disclosed in Japanese Patent Laid-open No. Sho 50-151997 Gazette]

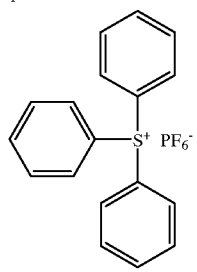

TEST EXAMPLE 2

Pigment-containing type curable composition)

(1) Photo curing Test 3 parts of a sulfonium salt compound and 1 part of a sensitizer were dissolve in a mixture of 100 parts of UVR-6110 (Alicyclic epoxy compound manufactured by UCC) and 100 parts of titanium dioxide (CR-58 manufactured by Ishihara Sangyo Kaisha), and the mixture was then kneaded by using a roller to prepare a composition. The composition obtained was applied onto a tin plate to form a film of the composition of 3 μm thickness, and the film was allowed to curing under the following condition. In this test, the composition which cured and became tack-free was represented by ○ mark, the composition which cured but remained tack or did not cure were represented by × mark in Table 3.

UV Irradiation Apparatus: HMW-450 manufactured by Oku Seisakusho

Lamp: Water-cooling type, 3 Kw-High-pressure mercury lamps

Dose of Irradiation: 200 mJ/cm²

(2) Heat Curing Test 0.5 g of the composition obtained as described above was weighed in a sample vessel, and the vessel was placed in an oven maintained at 150° C. for 30 minutes. After the heating, the composition which cured was represented by ○ mark, while the one which did not cure was represented by × mark. The result was shown in Table 3.

TABLE 3

| Sulfonium salt compound | Sensitizer | Photo curing | Heat Curing |
| --- | --- | --- | --- |
| Compound in Example 1 | 2,4-DETX | ○ | ○ |
| Compound in Example 4 | IPTX | ○ | ○ |
| Compound in Example 6 | EDMA | ○ | ○ |
| Compound in Example 7 | 2,4-DETX | ○ | ○ |
| Compound in Example 8 | 2,4-DMTX | ○ | ○ |
| Compound in Example 10 | 2,4-DMTX | ○ | ○ |
| Compound in Example 13 | 2,4-DMTX | ○ | ○ |
| Compound in Example 14 | 2,4-DMTX | ○ | ○ |
| Compound in Example 15 | 2,4-DMTX | ○ | ○ |
| Compound in Example 16 | 2,4-DMTX | ○ | ○ |
| Compound in Example 18 | 2,4-DMTX | ○ | ○ |
| Compound in Example 19 | 2,4-DMTX | ○ | ○ |
| Compound in Example 20 | 2,4-DMTX | ○ | ○ |
| Compound in Example 22 | 2,4-DMTX | ○ | ○ |
| Compound in Example 23 | 2,4-DMTX | ○ | ○ |
| Compound in Example 24 | 2,4-DMTX | ○ | ○ |
| Reference Example 1 | 2,4-DETX | × | ○ |
| Reference Example 2 | 2,4-DETX | × | × |
| Reference Example 3 | 2,4-DMTX | × | ○ |

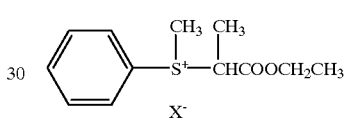

2,4-DETX: 2,4-diethylthio xanthone
2,4-DMTX: 2,4-dimethylthio xanthone
IPTX: Isopropylthio xanthone
EDMA: 2-ethyl-9,10-dimethoxy anthracene Industrial Use:

The sulfonium salt compounds according to the present invention are excellently active to heat and light and allow cationic polymerizable compounds to cure in a short time irrespective of their existing states such as films of which thickness being over a wide range from very thin to thick, under heating or irradiation of activation energy rays, such as light, electron rays and X-ray. The photo curing capability of the sulfonium salt compounds are further improved in combination with a sensitizer. Because of the capability to cure under a wavelength longer than 360 nm, the sulfonium salt compounds provide high curability even to pigment-containing compositions. Since the cured-product of such compositions show to have excellent physicochemical properties, those products can be preferably used for paints, adhesives, inks, photoresists, photosensitive resins for photomolding, etc.

What is claimed is:

1. A curable composition comprising a cationic polymerizable compound which is an alicyclic epoxy compound or a vinyl ether compound and a cationic polymerization initiator which is at least one sulfonium salt compound represented by a general formula I:

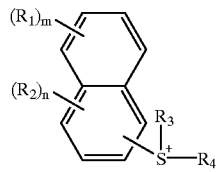

wherein $R_1$ and $R_2$ are each independently $C_{1-18}$ alkyl, $C_{1-18}$ alkoxy, $C_{1-18}$ alkylcarbonyl, benzoyloxy, phenylthio or halogeno;

$R_3$ is $C_{1-8}$ alkyl;

$R_4$ is (A) $C_{1-24}$ alkyl with no substituent or $R_4$ is (B) $C_{5-24}$ alkyl, $C_{2-24}$ alkenyl or $C_{3-20}$ cycloalkyl, wherein each of $R_4$ may contain a substituent selected from the group consisting of hydroxy, nitrile, phenyl, alkoxy, phenoxy, alkyleneoxy, halogen, indanyl, and carbonyl or $R_4$ is (c)

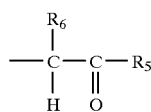

wherein $R_5$ is $C_{1-24}$ alkyl, $C_{2-24}$ alkenyl, $C_{3-20}$ cycloalkyl, $C_{1-24}$ alkoxy, phenyl, naphthyl or amino, wherein each of $R_5$ may contain a substitute selected from the group consisting of hydroxy, carbonyl, nitrile, alkoxy, phenoxy, alkyleneoxy, halogeno and nitro;

$R_6$ is hydrogen, $C_{1-8}$ alkyl or phenyl, or $R_5$ and $R_6$ may jointly form a ring which may optionally contain substituents selected from the group consisting of hydroxy, carbonyl, nitrile, phenyl, alkoxy, phenoxy and alkyleneoxy, or $R_5$ and $R_6$ may jointly form indanone, provided, if $R_6$ is not hydrogen, $R_5$ may be hydroxy;

m and n are each 0, 1, 2 or 3;

and X represents a non-nucleophilic anionic residue, the curable composition further comprising a sensitizer selected from the group consisting of naphthalene derivatives containing at least one hydroxy or alkoxy, thioxanthone derivatives or derivatives of 9,10-dialkoxy anthracene.

2. The curable composition according to claim 1 further comprising pigments.

3. The curable composition according to claim 2 containing titanium dioxide as the pigment.

4. The curable composition according to claim 1 wherein $R_4$ is

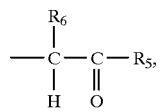

wherein $R_6$ is methyl or ethyl and $R_5$ is methoxy or ethoxy or

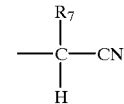

wherein $R_7$ is hydrogen, $C_{1-8}$ alkyl or phenyl.

5. A curable composition comprising:

(1) an alicyclic epoxy compound or a vinyl ether compound as a polymerizable compound, (2) a pigment, (3) at least one sulfonium salt compound represented by a general formula I:

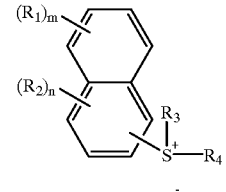

wherein $R_1$ and $R_2$ are each independently $C_{1-8}$ alkyl, $C_{1-18}$ alkoxy, $C_{1-18}$ alkylcarbonyl, benzoyloxy, phenylthio or halogeno;

$R_3$ is $C_{1-8}$ alkyl;

$R_4$ is (A) $C_{1-24}$ alkyl with no substituent or $R_4$ is (B) $C_{5-24}$ alkyl, $C_{2-24}$ alkenyl or $C_{3-20}$ cycloalkyl, wherein each of $R_4$ may contain a substituent selected from the group consisting of hydroxy, nitrile, phenyl, alkoxy, phenoxy, alkyleneoxy, halogen, indanyl, and carbonyl or $R_4$ is (c)

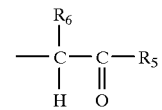

wherein $R_5$ is $C_{1-24}$ alkyl, $C_{2-24}$ alkenyl, $C_{3-20}$ cycloalkyl, $C_{1-24}$ alkoxy, phenyl, naphthyl or amino, wherein each of $R_5$ may contain a substitute selected from the group consisting of hydroxy, carbonyl, nitrile, alkoxy, phenoxy, alkyleneoxy, halogeno and nitro;

$R_6$ is hydrogen, $C_{1-8}$ alkyl or phenyl, or $R_5$ and $R_6$ may jointly form a ring which may optionally contain substituents selected from the group consisting of hydroxy, carbonyl, nitrile, phenyl, alkoxy, phenoxy and alkyleneoxy, or $R_5$ and $R_6$ may jointly form indanone, provided, if $R_6$ is not hydrogen, $R_5$ may be hydroxy;

m and n are each 0, 1, 2 or 3;

and X represents a non-nucleophilic anionic residue as a cationic polymerization initiator composition, and (4) at least one sensitizer selected from the group consisting of naphthalene derivatives containing at least one hydroxy or alkoxy, thioxanthone derivatives or derivatives of 9,10-dialkoxy anthracene.

6. A method of curing a curable composition according to claim 5 comprising exposing the composition to light from a gallium-containing lamp.

7. The curable composition according to claim 5 wherein $R_4$ is

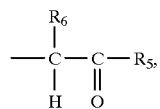

wherein $R_6$ is methyl or ethyl and $R_5$ is methoxy or ethoxy or

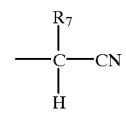

wherein $R_7$ is hydrogen, $C_{1-8}$ alkyl or phenyl.

* * * * *